US011158463B2

(12) United States Patent
Aoyama et al.

(10) Patent No.: US 11,158,463 B2
(45) Date of Patent: Oct. 26, 2021

(54) ELECTROLYTIC CAPACITOR AND METHOD FOR MANUFACTURING SAME

(71) Applicant: PANASONIC INTELLECTUAL PROPERTY MANAGEMENT CO., LTD., Osaka (JP)

(72) Inventors: Tatsuji Aoyama, Kyoto (JP); Kazuhiro Takatani, Hyogo (JP); Kazunari Imamoto, Yamaguchi (JP); Yoshiaki Ishimaru, Saga (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/681,397

(22) Filed: Nov. 12, 2019

(65) Prior Publication Data

US 2020/0079794 A1  Mar. 12, 2020

Related U.S. Application Data

(63) Continuation of application No. 15/963,233, filed on Apr. 26, 2018, now Pat. No. 10,593,486, which is a
(Continued)

(30) Foreign Application Priority Data

Nov. 27, 2015  (JP) .............................. JP2015-231293

(51) Int. Cl.
*H01G 9/00* (2006.01)
*H01G 9/028* (2006.01)
(Continued)

(52) U.S. Cl.
CPC ......... *H01G 9/0036* (2013.01); *C07D 513/04* (2013.01); *C07D 513/10* (2013.01);
(Continued)

(58) Field of Classification Search
CPC .... H01G 9/0036; H01G 9/0425; H01G 9/151; H01G 9/028; H01G 9/055
See application file for complete search history.

(56) References Cited

U.S. PATENT DOCUMENTS 7,643,270 B2 * 1/2010 Aoyama ................. H01G 9/04
                                                     361/532
10,453,618 B2 * 10/2019 Tsuda ................... H01G 9/0425
(Continued)

FOREIGN PATENT DOCUMENTS

CN       102831947 A    12/2012
CN       103380469 A    10/2013
(Continued)

OTHER PUBLICATIONS

English Translation of Chinese Search Report dated May 21, 2019 for the related Chinese Patent Application No. 201680067858.7.
(Continued)

*Primary Examiner* — Nathan Milakovich
(74) *Attorney, Agent, or Firm* — McDermott Will and Emery LLP

(57) ABSTRACT

An electrolytic capacitor includes a capacitor element, a solid electrolyte layer, and a liquid substance. The capacitor element includes an anode foil with a dielectric layer, and a cathode foil. The solid electrolyte layer is provided between the anode foil and the cathode foil. The capacitor element is impregnated with the liquid substance that includes a solvent and a solute. The solute contains one of an acid component, a nitro compound, or a phenol compound. The cathode foil includes a covering layer that contains at least one selected from the group consisting of titanium, nickel, a compound including titanium, and a compound including nickel. And the solid electrolyte layer contains a conductive polymer and a base component. An electrolytic capacitor includes a capacitor element, a solid electrolyte layer, and a liquid
(Continued)

substance. The capacitor element includes an anode foil with a dielectric layer, and a cathode foil. The solid electrolyte layer is provided between the anode foil and the cathode foil. The capacitor element is impregnated with the liquid substance that includes a solvent and a solute. The solute contains at least one selected from the group consisting of an acid component, a nitro compound, and a phenol compound. The cathode foil includes a covering layer that contains at least one selected from the group consisting of titanium, nickel, a compound including titanium, and a compound including nickel. And the solid electrolyte layer contains a conductive polymer and a base component.

8 Claims, 1 Drawing Sheet

Related U.S. Application Data continuation of application No. PCT/JP2016/004906, filed on Nov. 17, 2016.

(51) Int. Cl.
    *C07D 513/04*    (2006.01)
    *C07D 513/10*    (2006.01)
    *C07D 513/14*    (2006.01)
    *C07D 519/00*    (2006.01)
    *H01G 9/042*    (2006.01)
    *H01G 9/15*     (2006.01)
    *H01G 9/055*    (2006.01)

(52) U.S. Cl.
    CPC ......... *C07D 513/14* (2013.01); *C07D 519/00* (2013.01); *H01G 9/028* (2013.01); *H01G 9/0425* (2013.01); *H01G 9/151* (2013.01); *H01G 9/055* (2013.01)

(56) References Cited

U.S. PATENT DOCUMENTS

| | | | |
|---|---|---|---|
| 2006/0047030 A1 | 3/2006 | Yoshida et al. | |
| 2009/0021894 A1* | 1/2009 | Ning | H01G 9/025 361/527 |
| 2009/0109602 A1 | 4/2009 | Kakuma et al. | |
| 2009/0144954 A1 | 6/2009 | Furusawa et al. | |
| 2013/0294013 A1 | 11/2013 | Ning et al. | |
| 2013/0330617 A1* | 12/2013 | Yoshimura | H01G 11/32 429/211 |
| 2015/0213962 A1 | 7/2015 | Koseki et al. | |
| 2016/0217934 A1 | 7/2016 | Tsuda et al. | |
| 2017/0053745 A1 | 2/2017 | Aoyama et al. | |
| 2019/0006111 A1 | 1/2019 | Tsubaki et al. | |
| 2019/0013152 A1 | 1/2019 | Aoyama et al. | |
| 2020/0105479 A1* | 4/2020 | Matsushita | H01G 9/0032 |
| 2020/0203081 A1* | 6/2020 | Saito | H01G 9/028 |
| 2021/0098199 A1* | 4/2021 | Tsuda | H01G 11/48 |

FOREIGN PATENT DOCUMENTS

| | | | |
|---|---|---|---|
| JP | 2004-128048 A | | 4/2004 |
| JP | 2008-066502 A | | 3/2008 |
| JP | 2009-111174 A | | 5/2009 |
| JP | 2009-289833 A | | 12/2009 |
| JP | 2010-123924 A | | 6/2010 |
| JP | 2012-174865 A | | 9/2012 |
| JP | 2014-007401 A | | 1/2014 |
| JP | 2014-027040 A | | 2/2014 |
| JP | 2014-067949 A | | 4/2014 |
| JP | 2015-103743 A | | 6/2015 |
| JP | 2015103743 A | * | 6/2015 |
| WO | 2007/091656 A1 | | 8/2007 |
| WO | 2015/059913 A1 | | 4/2015 |
| WO | 2015/174056 A1 | | 11/2015 |

OTHER PUBLICATIONS

International Search Report of PCT application No. PCT/JP2016/004906 dated Jan. 31, 2017; with English translation.
Non-Final Office Action issued in U.S. Appl. No. 15/963,233, dated Apr. 5, 2019.
Notice of Allowance issued in U.S. Appl. No. 15/963,233, dated Aug. 14, 2019.

* cited by examiner

ELECTROLYTIC CAPACITOR AND METHOD FOR MANUFACTURING SAME

CROSS-REFERENCE OF RELATED APPLICATIONS

This application is a Continuation of U.S. patent application Ser. No. 15/963,233, filed on Apr. 26, 2018, which is a Continuation of International Patent Application No. PCT/JP2016/004906, filed on Nov. 17, 2016, which in turn claims the benefit of Japanese Application No. 2015-231293, filed on Nov. 27, 2015, the entire disclosures of which Applications are incorporated by reference herein.

TECHNICAL FIELD

The present disclosure relates to an electrolytic capacitor including a solid electrolyte layer and an electrolyte solution, and a method for manufacturing the electrolytic capacitor.

BACKGROUND

As a capacitor having a small size, a large capacitance, and low ESR (Equivalent Series Resistance), one of promising candidates is an electrolytic capacitor including an anode foil on which a dielectric layer is formed, a solid electrolyte layer formed so as to cover at least a part of the dielectric layer, and an electrolyte solution. For example, Unexamined Japanese Patent Publication No. 2009-111174 discloses an electrolytic capacitor obtained by impregnating a solid electrolyte layer with a solvent containing, for example, γ-butyrolactone or sulfolane.

Further, for example, Unexamined Japanese Patent Publication No. 2004-128048 discloses an electrolytic capacitor including an anode foil, a solid electrolyte layer, and a cathode foil on which a coating film made of a metal nitride or a metal is formed.

SUMMARY

An electrolytic capacitor according to the present disclosure includes a capacitor element, a solid electrolyte layer, and a liquid substance. The capacitor element has an anode foil with a dielectric layer, and a cathode foil. The solid electrolyte layer is provided between the anode foil and the cathode foil. The capacitor element is impregnated with the liquid substance that includes a solvent and a solute. The solute contains one selected from the group consisting of an acid component, a nitro compound, and a phenol compound. The cathode foil includes a covering layer that contains at least one selected from the group consisting of titanium, nickel, a compound including titanium, and a compound including nickel. And the solid electrolyte layer contains a conductive polymer and a base component.

According to the present disclosure, there can be provided an electrolytic capacitor having a high electrostatic capacity and low ESR.

DESCRIPTION OF EMBODIMENT

In the conventional electrolytic capacitor including a solid electrolyte layer and an electrolyte solution, there is a problem that neither a sufficiently high electrostatic capacity nor low ESR might be obtain by forming the solid electrolyte layer with use of a dispersion containing a conductive polymer even when a titanium coating film is formed on a cathode foil.

In order to solve the problem, the present disclosure provides an electrolytic capacitor having a high electrostatic capacity and low ESR.

Hereinafter, the present disclosure is more specifically described with reference to an exemplary embodiment. The exemplary embodiment below, however, is not to limit the present disclosure.

Figure 1:
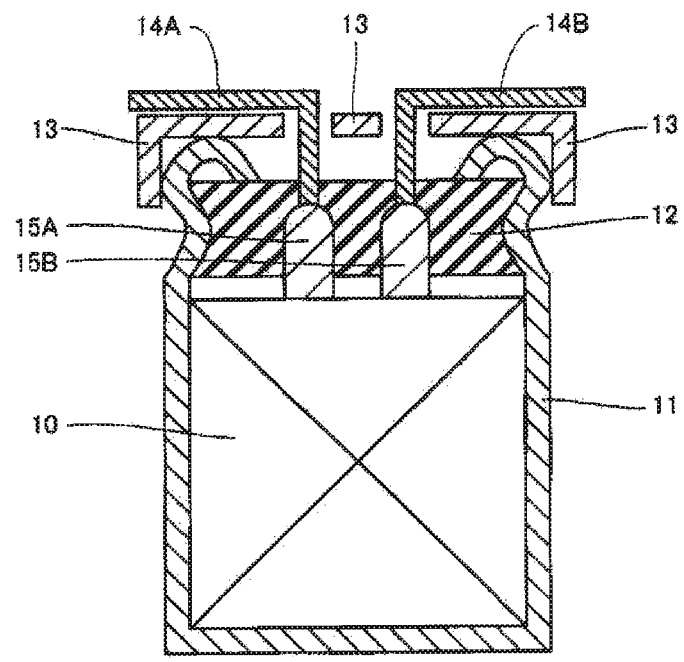
FIG. 1 is a schematic sectional view illustrating an electrolytic capacitor according to one exemplary embodiment of the present disclosure.
Figure 2:
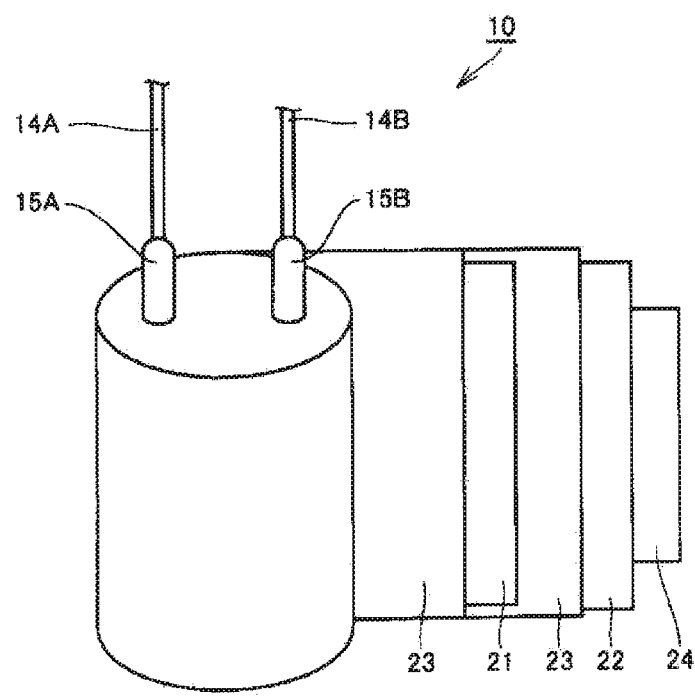
FIG. 2 is a schematic view illustrating a configuration of a capacitor element according to the exemplary embodiment.

FIG. 1 is a schematic sectional view illustrating an electrolytic capacitor according to the present exemplary embodiment, and FIG. 2 is a schematic view obtained by developing a part of a capacitor element of the electrolytic capacitor.

The electrolytic capacitor includes, for example, capacitor element 10, bottomed case 11 that houses capacitor element 10, sealing member 12 that seals an opening of bottomed case 11, base plate 13 that covers sealing member 12, lead wires 14A, 14B that are lead out from sealing member 12 and penetrate base plate 13, lead tabs 15A, 15B that connect the lead wires to electrodes of capacitor element 10, respectively, and an electrolyte solution (not shown). Bottomed case 11 is, at a part near an opening end, processed inward by drawing, and is, at the opening end, curled to swage sealing member 12.

Capacitor element 10 includes anode foil 21 connected to lead tab 15A, cathode foil 22 connected to lead tab 15B, and separator 23.

Anode foil 21 and cathode foil 22 are wound with separator 23 interposed between the anode foil and the cathode foil. An outermost periphery of capacitor element 10 is fixed with fastening tape 24. FIG. 2 shows partially developed capacitor element 10 before the outermost periphery of the capacitor element is fixed.

Anode foil 21 includes a metal foil whose surface is roughened so as to have projections and recesses, and a dielectric layer is formed on the metal foil having the projections and recesses. A conductive polymer is attached to at least a part of a surface of the dielectric layer to form a solid electrolyte layer. The solid electrolyte layer may cover at least a part of a surface of cathode foil 22 and/or at least a part of a surface of separator 23. Capacitor element 10 in which the solid electrolyte layer has been formed is housed in bottomed case 11 together with the electrolyte solution.

An electrolytic capacitor according to the present disclosure includes an anode foil with a dielectric layer; a cathode foil; a solid electrolyte layer in contact with the dielectric layer; and an electrolyte solution. The cathode foil includes a covering layer containing at least one metal selected from titanium and nickel or a compound of the at least one metal. The solid electrolyte layer contains a conductive polymer, a polymer dopant, and a base component.

<<Method for Manufacturing Electrolytic Capacitor>>

Hereinafter, described are steps of one exemplary method for manufacturing the electrolytic capacitor according to the present exemplary embodiment.

(i) Step of Preparing Anode Foil 21 with Dielectric Layer

First, a metal foil as a raw material for anode foil 21 is prepared. A type of the metal is not particularly limited, but it is preferred to use a valve metal such as aluminum, tantalum, or niobium, or an alloy containing a valve metal, from the viewpoint of facilitating formation of a dielectric layer.

Next, a surface of the metal foil is roughened. By the roughening, a plurality of projections and recesses are formed on the surface of the metal foil. The roughening is preferably performed by etching the metal foil. The etching may be performed by, for example, a direct-current electrolytic method or an alternating-current electrolytic method.

Next, a dielectric layer is formed on the roughened surface of the metal foil. A method for forming the dielectric layer is not particularly limited, and the dielectric layer can be formed by subjecting the metal foil to an anodizing treatment. The anodizing treatment is performed by, for example, immersing the metal foil in an anodizing solution such as an ammonium adipate solution, followed by a heat treatment. The anodizing treatment may also be performed by applying a voltage to the metal foil that has been immersed in the anodizing solution.

Normally, a large foil of, for example, a valve metal (metal foil) is subjected to the roughening treatment and the anodizing treatment from the viewpoint of mass productivity. In this case, the treated foil is cut into a desired size to prepare anode foil 21.

(ii) Step of Preparing Cathode Foil 22

Next, cathode foil 22 including a metal foil and a covering layer formed on a surface of the metal foil is prepared. Cathode foil 22 including the covering layer can increase an electrostatic capacity of a capacitor. A type of the metal that constitutes the metal foil is not particularly limited, but it is preferred to use a valve metal such as aluminum, tantalum, or niobium, or an alloy containing a valve metal. The surface of the metal foil may be roughened as necessary before formation of the covering layer.

The covering layer contains at least one metal selected from titanium and nickel or a compound of the at least one metal. As the metal compound, there can be used a nitride and a carbide. The covering layer may also include a layer containing carbon on a surface of the covering layer. On the other hand, a cathode foil obtained by fixing carbon particles as aluminum carbide on a surface of an aluminum foil is not preferred because aluminum carbide is hydrolyzed by a little amount of moisture contained in an electrolyte solution described later. As a method for forming the covering layer, there can be used gas phase methods such as a vacuum deposition method, a chemical vapor deposition method, a sputtering method, and an ion plating method.

(iii) Production of Capacitor Element 10

Next, capacitor element 10 is produced with use of anode foil 21 and cathode foil 22. First, anode foil 21 and cathode foil 22 are wound with separator 23 interposed between the anode foil and the cathode foil. At this time, the winding can be conducted while lead tabs 15A, 15B are rolled in the anode foil, the cathode foil, and the separator, to cause lead tabs 15A, 15B to stand up from capacitor element 10 as illustrated in FIG. 2.

As a material for separator 23, a nonwoven fabric can be used that includes, as a main component, for example, cellulose, polyethylene terephthalate, polyacrylonitrile, vinylon, or an aramid fiber.

A material for lead tabs 15A, 15B is not particularly limited as long as the material is a conductive material. A material for lead wires 14A, 14B connected to lead tabs 15A, 15B, respectively, is not also particularly limited as long as the material is a conductive material.

Next, fastening tape 24 is disposed on an outer surface of cathode foil 22 positioned at an outermost layer of wound anode foil 21, cathode foil 22, and separator 23, to fix an end of cathode foil 22 with fastening tape 24. When anode foil 21 is prepared by cutting a large metal foil, the wound body may further be subjected to an anodizing treatment in order to provide a dielectric layer on a cutting surface of anode foil 21.

(iv) Step of Forming Solid Electrolyte Layer

Next, the dielectric layer is impregnated with a polymer dispersion to form a film covering at least a part of the dielectric layer. The polymer dispersion contains a solvent, a conductive polymer, a polymer dopant, and a base component. The polymer dispersion may be a solution obtained by dissolving the conductive polymer in the solvent, or a dispersion liquid obtained by dispersing particles of the conductive polymer in the solvent. Next, the solvent is volatilized from the formed film by drying, and then a dense solid electrolyte layer covering at least a part of the dielectric layer is formed. In the polymer dispersion, the conductive polymer is uniformly distributed in the solvent to easily form a uniform solid electrolyte layer. Thus, capacitor element 10 can be obtained.

As the base component, it is preferred to use, for example, ammonia, a primary to tertiary amine, a quaternary ammonium, and a quaternized amidinium. As the primary to tertiary amine, there can be used, for example, methylamine, dimethylamine, trimethylamine, ethylamine, diethylamine, triethylamine, ethylenediamine, N,N-diisopropylethylamine, tetramethylethylenediamine, and hexamethylenediamine. As the quaternary ammonium, there can be used, for example, tetramethylammonium, triethylmethylammonium, and tetraethylammonium. As the quaternized amidinium, there can be used, for example, ethyldimethylimidazolinium and tetramethylimidazolinium.

A polymer dispersion containing no base component has lower wettability to a cathode foil that includes a covering layer containing, for example, titanium, nickel, or carbon than to a cathode foil that includes an anodizing coating film. Therefore, the polymer dispersion containing no base component gives insufficient adhesiveness between a resultant solid electrolyte layer and the cathode foil and/or insufficient covering properties, so that the electrostatic capacity and the ESR of a capacitor might be deteriorated. On the other hand, a polymer dispersion containing a base component has high wettability to a cathode foil including the covering layer. Therefore, the polymer dispersion containing a base component gives good adhesiveness between a resultant solid electrolyte layer and the cathode foil, and good covering properties, so that the electrostatic capacity and the ESR of a capacitor can be improved. The polymer dispersion can be obtained by, for example, a method for dispersing the conductive polymer in a liquid component or a method for polymerizing a precursor monomer in a liquid component and generating particles of the conductive polymer.

The conductive polymer is preferably, for example, polypyrrole, polythiophene, or polyaniline. These conductive polymers may be used alone, or two or more of the conductive polymers may be used in combination, or a copolymer of two or more monomers may be used. A resultant solid electrolyte layer containing such a conductive polymer can be expected to further improve withstand voltage characteristics.

In the present specification, polypyrrole, polythiophene, polyaniline, and the like mean polymers having, as a basic skeleton, polypyrrole, polythiophene, polyaniline, and the like, respectively. Therefore, polypyrrole, polythiophene, polyaniline, and the like can also include derivatives of polypyrrole, polythiophene, polyaniline, and the like, respectively. For example, polythiophene includes poly(3, 4-ethylenedioxythiophene) (PEDOT) and the like.

Examples of the polymer dopant include polyanions of polyvinylsulfonic acid, polystyrenesulfonic acid, polyallylsulfonic acid, polyacrylsulfonic acid, polymethacrylsulfonic acid, poly(2-acrylamido-2-methylpropanesulfonic acid), polyisoprenesulfonic acid, and polyacrylic acid. These polymer dopants may be used alone, or two or more of the dopants may be used in combination. These polymer dopants may be a homopolymer or a copolymer of two or more monomers. Especially, polystyrenesulfonic acid (PSS) is preferred.

A weight average molecular weight of the polymer dopant is not particularly limited but preferably ranges, for example, from 1000 to 500000, inclusive, in terms of facilitating formation of a homogeneous solid electrolyte layer.

The solvent may be water, a mixture of water and a nonaqueous solvent, or a nonaqueous solvent. The nonaqueous solvent is not particularly limited, and a protic solvent and an aprotic solvent can be used, for example. Examples of the protic solvent include alcohols such as methanol, ethanol, propanol, butanol, ethylene glycol, propylene glycol, and a polyalkylene glycol, formaldehyde, and ethers such as 1,4-dioxane. Examples of the aprotic solvent include amides such as N-methylacetamide, N,N-dimethylformamide, and N-methyl-2-pyrrolidone, esters such as methyl acetate, and ketones such as methyl ethyl ketone.

A concentration of the conductive polymer contained in the polymer dispersion preferably ranges from 0.5% by mass to 10% by mass, inclusive. An average particle diameter D50 of the conductive polymer preferably ranges, for example, from 0.01 µm to 0.5 µm, inclusive. Here, the average particle diameter D50 is a median diameter in a volume particle size distribution obtained by a particle size distribution measuring apparatus according to dynamic light scattering. The polymer dispersion having such a concentration is suitable for forming a solid electrolyte layer having an appropriate thickness and is easily impregnated into the dielectric layer.

A concentration of the base component contained in the polymer dispersion ranges preferably from 0.001 mol/kg to 0.04 mol/kg, inclusive, particularly preferably from 0.003 mol/kg to 0.03 mol/kg, inclusive.

As a method for applying the polymer dispersion to a surface of the dielectric layer, for example, a method for immersing the wound body in the polymer dispersion housed in a container is simple and preferred. An immersion period depends on a size of the wound body and ranges, for example, from 1 second to 5 hours, inclusive, preferably from 1 minute to 30 minutes, inclusive. In addition, impregnation is preferably performed under a reduced pressure, in an atmosphere ranging, for example, from 10 kPa to 100 kPa, inclusive, preferably from 40 kPa to 100 kPa, inclusive. Further, ultrasonic vibration may be applied to the wound body or the polymer dispersion while the wound body is immersed in the polymer dispersion. The drying after picking the wound body up from the polymer dispersion is preferably performed at a temperature ranging from 50° C. to 300° C., inclusive, more preferably from 100° C. to 200° C., inclusive, for example.

The step of applying the polymer dispersion to the surface of the dielectric layer and the step of drying capacitor element 10 may be repeated two or more times. These steps can be performed a plurality of times to increase coverage of the solid electrolyte layer on the dielectric layer. In the formation, the solid electrolyte layer may be formed on not only the surface of the dielectric layer but also surfaces of cathode foil 22 and separator 23.

As described above, the solid electrolyte layer is formed between anode foil 21 and cathode foil 22. The solid electrolyte layer formed on the surface of the dielectric layer actually functions as a cathode material.

(v) Step of Impregnating Capacitor Element 10 with Electrolyte Solution

Next, capacitor element 10 is impregnated with an electrolyte solution. A method for impregnating capacitor element 10 with the electrolyte solution is not particularly limited. For example, a method for immersing capacitor element 10 in the electrolyte solution housed in a container is simple and preferred. An immersion period depends on a size of capacitor element 10 and ranges, for example, from 1 second to 5 minutes, inclusive. Impregnation is preferably performed under a reduced pressure, in an atmosphere ranging, for example, from 10 kPa to 100 kPa, inclusive, preferably from 40 kPa to 100 kPa, inclusive.

The electrolyte solution can contain, for example, a polyhydric alcohol, a sulfone compound, a lactone compound, a carbonate compound, and a monohydric alcohol. These alcohols and compounds may be used alone or in combination of a plurality of alcohols and compounds.

The polyhydric alcohol desirably includes at least one of ethylene glycol, diethylene glycol, triethylene glycol, propylene glycol, butane diol, a polyalkylene glycol, or glycerol, for example. As the polyalkylene glycol, it is preferred to use polyethylene glycol having an average molecular weight ranging from 200 to 1000, inclusive, or polypropylene glycol having an average molecular weight ranging from 200 to 5000, inclusive.

As the lactone compound, there can be used, for example, γ-butyrolactone and γ-valerolactone. As to the carbonate compound, the electrolyte solution can contain, as a solvent, dimethyl carbonate, diethyl carbonate, ethyl methyl carbonate, ethylene carbonate, propylene carbonate, and fluoroethylene carbonate, for example. Particularly, it is desired to use ethylene glycol, a polyalkylene glycol, γ-butyrolactone, and sulfolane.

The electrolyte solution may also contain a solute. As the solute, there can be used, for example, an acid component, a base component, a salt of an acid component and a base component, a nitro compound, and a phenol compound.

As the acid component, there can be used an organic acid, an inorganic acid, and a composite compound of an organic acid and an inorganic acid. As the organic acid, there can be used, for example, phthalic acid, isophthalic acid, terephthalic acid, maleic acid, adipic acid, benzoic acid, and carboxylic acids such as 1,6-decanedicarboxylic acid, 1,7-octanedicarboxylic acid, and azelaic acid. As the inorganic acid, there can be used, for example, boric acid, phosphoric acid, phosphorous acid, hypophosphorous acid, and a phosphate ester.

As the composite compound of an organic acid and an inorganic acid, there can be used, for example, borodisalicylic acid, borodioxalic acid, and borodiglycolic acid.

As the base component, there can be used, for example, a primary to tertiary amine, a quaternary ammonium, and a quaternized amidinium. As the primary to tertiary amine, there can be used, for example, methylamine, dimethylamine, trimethylamine, ethylamine, diethylamine, triethylamine, ethylenediamine, N,N-diisopropylethylamine, tetramethylethylenediamine, and hexamethylenediamine. As the quaternary ammonium, there can be used, for example, tetramethylammonium, triethylmethylammonium, and tetraethylammonium. As the quaternized amidinium, there can be used, for example, ethyldimethylimidazolinium and tetramethylimidazolinium.

A proportion of the solute contained in the electrolyte solution desirably ranges from 0% by mass to 30% by mass, inclusive. When the proportion of the solute is in this range, an increase in viscosity of the electrolyte solution is small, and a voltage is less likely to decrease.

(vi) Step of Encapsulating Capacitor Element

Next, capacitor element 10 is encapsulated. Specifically, first, capacitor element 10 is housed in bottomed case 11 so that lead wires 14A, 14B are positioned on an open upper surface of bottomed case 11. As a material for bottomed case 11, there can be used metals such as aluminum, stainless steel, copper, iron and brass, or alloys of these metals.

Next, sealing member 12 formed so as to allow lead wires 14A, 14B to penetrate the sealing member is disposed above capacitor element 10 so as to encapsulate capacitor element 10 in bottomed case 11. Next, bottomed case 11 is, at a part near an opening end, processed by transverse drawing, and is, at the opening end, curled to swage sealing member 12. Then, base plate 13 is disposed on a curled part of the bottomed case to complete the electrolytic capacitor as illustrated in FIG. 1. Then, an aging treatment may be performed while a voltage is applied.

Sealing member 12 is formed of an elastic material containing a rubber component. As the rubber component, there can be used a butyl rubber (IIR), a nitrile rubber (NBR), an ethylene propylene rubber, an ethylene propylene diene rubber (EPDM), a chloroprene rubber (CR), an isoprene rubber (IR), a Hypalon (trademark) rubber, a silicone rubber, and a fluorine-containing rubber. Sealing member 12 may contain fillers such as carbon black and silica.

EXAMPLES

Hereinafter, the present disclosure is described in more detail with reference to examples. The present disclosure, however, is not to be considered to be limited to the examples.

Example 1

In the present example, a wound electrolytic capacitor having a rated voltage of 35 V and a rated electrostatic capacity of 330 µF was produced. Hereinafter, a specific method for manufacturing the electrolytic capacitor is described.

(Preparation of Anode Foil)

A 100-µm-thick aluminum foil was subjected to etching to roughen a surface of the aluminum foil. Then, a dielectric layer was formed on the surface of the aluminum foil by an anodizing treatment. The anodizing treatment was performed by immersing the aluminum foil in an ammonium adipate solution and applying a voltage to the aluminum foil. Then, the aluminum foil was cut into a size of 6 mm (length)×120 mm (width) to prepare an anode foil.

(Preparation of Cathode Foil)

A 50-µm-thick aluminum foil was subjected to etching, and a titanium layer and a carbon layer were sequentially formed as a covering layer. Then, the aluminum foil was cut into a size of 6 mm (length)×120 mm (width) to prepare a cathode foil.

(Production of Capacitor Element)

An anode lead tab and a cathode lead tab were connected to the anode foil and the cathode foil, respectively, and the anode foil and the cathode foil were wound with a separator interposed between the anode foil and the cathode foil while the lead tabs were rolled in the anode foil, the cathode foil, and the separator. Ends of the lead tabs protruding from a wound body were connected to an anode lead wire and a cathode lead wire, respectively. Then, the produced wound body was subjected to an anodizing treatment again to form a dielectric layer at a cutting end of the anode foil. Next, an end of an outer surface of the wound body was fixed with a fastening tape to produce a capacitor element.

(Preparation of Polymer Dispersion)

A mixed solution was prepared by dissolving 3,4-ethylenedioxythiophene and polystyrenesulfonic acid (PSS, weight average molecular weight 100000) in ion-exchanged water (liquid component). While the mixed solution was stirred, iron (III) sulfate (oxidant) that had been dissolved in ion-exchanged water was added to the mixed solution to cause a polymerization reaction. After the reaction, a resultant reaction solution was dialyzed to remove unreacted monomers and an excessive oxidant, so that a polymer dispersion was obtained that contained about 2% by mass of polyethylene dioxythiophene doped with PSS (PEDOT/PSS). Then, ammonia was added as a base component in an amount of 0.02 mol with respect to 1 kg of the polymer dispersion.

(Formation of Solid Electrolyte Layer)

The capacitor element was immersed in the polymer dispersion housed in a predetermined container in a reduced-pressure atmosphere (40 kPa) for 5 minutes, and then the capacitor element was picked up from the polymer dispersion. Next, the capacitor element that had been impregnated with the polymer dispersion was dried in a drying furnace at 150° C. for 20 minutes so as to form a solid electrolyte layer covering at least a part of the dielectric layer.

(Impregnation with Electrolyte Solution)

An electrolyte solution was prepared that contained 40% by mass of γ-butyrolactone, 40% by mass of sulfolane, and 20% by mass of ethyldimethylamine phthalate, and the capacitor element was immersed in the electrolyte solution for 5 minutes in a reduced-pressure atmosphere (40 kPa).

(Encapsulation of Capacitor Element)

The capacitor element that had been impregnated with the electrolyte solution was encapsulated to complete an electrolytic capacitor. Specifically, the capacitor element was housed in a bottomed case so that lead wires were positioned on an opening side of the bottomed case. And a sealing member (an elastic material including a butyl rubber as a rubber component) that was formed so as to allow the lead wires to penetrate the sealing member was disposed above the capacitor element, so as to encapsulate the capacitor element in the bottomed case. The bottomed case was, at a part near an opening end, processed by drawing and was further curled at the opening end, and a base plate was disposed on a curled part to complete the electrolytic capacitor as illustrated in FIG. 1. Thereafter, an aging treatment was performed at 130° C. for 2 hours while a rated voltage was applied.

Example 2

An electrolytic capacitor was produced in the same manner as in Example 1 except that diethylamine was used as the base component, and the evaluation was performed in the same manner.

Example 3

An electrolytic capacitor was produced in the same manner as in Example 1 except that diethanolamine was used as the base component, and the evaluation was performed in the same manner.

Example 4

An electrolytic capacitor was produced in the same manner as in Example 1 except that dimethylaminoethanol was used as the base component, and the evaluation was performed in the same manner.

Example 5

An electrolytic capacitor was produced in the same manner as in Example 1 except that ammonia was added in an amount of 0.001 mol with respect to 1 kg of the polymer dispersion, and the evaluation was performed in the same manner.

Example 6

An electrolytic capacitor was produced in the same manner as in Example 1 except that ammonia was added in an amount of 0.003 mol with respect to 1 kg of the polymer dispersion, and the evaluation was performed in the same manner.

Example 7

An electrolytic capacitor was produced in the same manner as in Example 1 except that ammonia was added in an amount of 0.03 mol with respect to 1 kg of the polymer dispersion, and the evaluation was performed in the same manner.

Example 8

An electrolytic capacitor was produced in the same manner as in Example 1 except that ammonia was added in an amount of 0.04 mol with respect to 1 kg of the polymer dispersion, and the evaluation was performed in the same manner.

Example 9

An electrolytic capacitor was produced in the same manner as in Example 1 except that a titanium nitride layer was formed as the covering layer in place of the titanium layer and the carbon layer, and the evaluation was performed in the same manner.

Example 10

An electrolytic capacitor was produced in the same manner as in Example 1 except that a nickel layer was formed as the covering layer in place of the titanium layer and the carbon layer, and the evaluation was performed in the same manner.

Comparative Example 1

An electrolytic capacitor was produced in the same manner as in Example 1 except that a cathode foil was used that included, in place of the covering layer, a anodizing coating film formed through anodizing at 2 V, and the evaluation was performed in the same manner.

Comparative Example 2

An electrolytic capacitor was produced in the same manner as in Example 1 except that no base component was added to the polymer dispersion, and the evaluation was performed in the same manner.

[Evaluation]

An electrostatic capacity ($\mu F$) was measured for the electrolytic capacitors. Specifically, an electrostatic capacity ($\mu F$) at a frequency of 120 Hz was measured for the electrolytic capacitors with an LCR meter for 4-terminal measurement. An ESR value ($m\Omega$) was also measured for the electrolytic capacitors. Specifically, an ESR value ($m\Omega$) at a frequency of 100 kHz was measured for the electrolytic capacitors with an LCR meter for 4-terminal measurement. The electrostatic capacity and the ESR value were each measured for randomly selected 120 electrolytic capacitors, and average values for the electrostatic capacity and the ESR value were calculated.

TABLE 1

|  | Electrostatic capacity ($\mu F$) | ESR ($m\Omega$) |
| --- | --- | --- |
| Example 1 | 331.55 | 9.1 |
| Example 2 | 322.79 | 10.1 |
| Example 3 | 323.87 | 9.4 |
| Example 4 | 324.99 | 10.3 |
| Example 5 | 328.12 | 15.8 |
| Example 6 | 329.84 | 12.6 |
| Example 7 | 332.01 | 11.9 |
| Example 8 | 334.89 | 13.1 |
| Example 9 | 330.55 | 10.1 |
| Example 10 | 321.56 | 10.9 |
| Comparative Example 1 | 251.21 | 13.8 |
| Comparative Example 2 | 301.88 | 57.8 |

The present disclosure can be utilized for an electrolytic capacitor that includes a solid electrolyte layer covering at least a part of a dielectric layer, and an electrolyte solution.

What is claimed is:

1. An electrolytic capacitor comprising:
   a capacitor element including an anode foil and a cathode foil, the anode foil including a dielectric layer;
   a solid electrolyte layer provided between the anode foil and the cathode foil; and
   a liquid substance with which the capacitor element is impregnated, the liquid substance including a solvent and a solute, the solute containing one selected from the group consisting of an acid component, a nitro compound, and a phenol compound, wherein:
   the cathode foil includes a metal foil and a covering layer disposed on a surface of the metal foil, the covering layer containing at least one selected from the group consisting of titanium, nickel, a compound including titanium, and a compound including nickel, and
   the solid electrolyte layer contains a conductive polymer and a base component.

2. The electrolytic capacitor according to claim 1, wherein the base component includes at least one selected from the group consisting of ammonia, a primary to tertiary amine, a quaternary ammonium, and a quaternized amidinium.

3. The electrolytic capacitor according to claim 1, wherein the covering layer includes a carbon layer.

4. The electrolytic capacitor according to claim 1, wherein the solvent includes at least one selected from the group consisting of a polyhydric alcohol, a sulfone compound, a lactone compound, a carbonate compound, and a monohydric alcohol.

5. The electrolytic capacitor according to claim 1, wherein the acid component includes one selected from the group consisting of an organic acid, an inorganic acid, and a composite compound of an organic acid and an inorganic acid.

6. The electrolytic capacitor according to claim 5, wherein the organic acid includes one selected from the group consisting of phthalic acid, isophthalic acid, terephthalic acid, maleic acid, adipic acid, benzoic acid, and carboxylic acid.

7. The electrolytic capacitor according to claim 5, wherein the inorganic acid includes one selected from the group consisting of boric acid, phosphoric acid, phosphorous acid, hypophosphorous acid, and a phosphate ester.

8. The electrolytic capacitor according to claim 5, wherein the composite compound of an organic acid and an inorganic acid includes one selected from the group consisting of borodisalicylic acid, borodioxalic acid, and borodiglycolic acid.

* * * * *